US011357184B2

(12) United States Patent
Quintana et al.

(10) Patent No.: US 11,357,184 B2
(45) Date of Patent: Jun. 14, 2022

(54) METHOD OF COMBINING FUSARIUM RESISTANCE AND PEPPER

(71) Applicant: SAKATA SEED AMERICA, INC., Morgan Hill, CA (US)

(72) Inventors: Juan Manuel Quintana, Guamuchil (MX); Marco Hernandez Bello, Alva, FL (US); Suraj Gurung, Pacific Grove, CA (US); Tatiana Simkova, Aptos, CA (US)

(73) Assignee: Sakata Seed America, Inc., Morgan Hill, CA (US)

( * ) Notice: Subject to any disclaimer, the term of this patent is extended or adjusted under 35 U.S.C. 154(b) by 0 days.

(21) Appl. No.: 16/599,345

(22) Filed: Oct. 11, 2019

(65) Prior Publication Data

US 2020/0115720 A1 Apr. 16, 2020

Related U.S. Application Data

(60) Provisional application No. 62/744,714, filed on Oct. 12, 2018.

(51) Int. Cl.

| | |
|---|---|
| ***A01H 1/04*** | (2006.01) |
| ***C12N 15/82*** | (2006.01) |
| ***A01H 5/08*** | (2018.01) |
| ***A01H 6/82*** | (2018.01) |

(52) U.S. Cl.

CPC ................. *A01H 1/04* (2013.01); *A01H 5/08* (2013.01); *A01H 6/822* (2018.05); *C12N 15/8282* (2013.01)

(58) Field of Classification Search

None

See application file for complete search history.

(56) References Cited

U.S. PATENT DOCUMENTS

| | | | | |
|---|---|---|---|---|
| 5,262,316 | A | 11/1993 | Engler et al. | |
| 5,523,520 | A | 6/1996 | Hunsperger et al. | |
| 9,351,452 | B2 | 5/2016 | de Bloois | |
| 9,723,797 | B2 | 8/2017 | Braun et al. | |
| 9,795,098 | B2 | 10/2017 | de Bloois | |
| 9,832,946 | B2 | 12/2017 | Tarekegn | |
| 9,924,651 | B2 | 3/2018 | Vreugdenhil | |
| 10,051,805 | B1 * | 8/2018 | Sharma | A01H 5/08 |
| 2015/0037893 | A1 | 2/2015 | Ausubel et al. | |
| 2017/0275708 | A1 | 9/2017 | Broglie et al. | |
| 2018/0245091 | A1 | 8/2018 | Caldwell et al. | |

FOREIGN PATENT DOCUMENTS

| | | | |
|---|---|---|---|
| WO | PCT/US2019/055864 | | 10/2019 |
| WO | WO 2020/077224 | A1 | 4/2020 |

OTHER PUBLICATIONS

Lomas-Cano et al. Phytoparasitica (2016) 44:283-293.*

Geiser et al. European Journal of Plant Pathology (2004), 110:473-479.*

Bernacchi et al . Theor Appl Genet(1998) 97:381-397.*

Allard, R.W., Breeding Self-Pollinated Plants, Principles of Plant Breeding, $2^{nd}$ ed., John Wiley & Sons, Inc., 1999, pp. 175-197.

Altpeter, F., et al., Advancing Crop Transformation in the Era of Genome Editing, *The Plant Cell*, 2016, 28:1510-1520.

Anaya-Lopez, J.L., et al., Selection of chili pepper genotypes resistant to pathogenic wilt disease complex, *Revista Mexicana de Ciencias Agricolas*, 2011, 2(3):373-383.

Bashir, M.R., et al., Management of Fusarium wilt of chilli caused by *Fusarium oxysporum* f.sp. *capsici* through nutritional amendments under greenhouse conditions, *International Journal of Biosciences*, 2017, 10(3):185-191.

Bennetzen, J.L. and Jones, J.D.G., edited by Setlow, J.K., Approaches and progress in the molecular cloning of plant disease resistance genes, *Genetic Engineering*, 1992, 14:99-124.

Cerkauskas, R.F., Etiology and management of Fusarium crown and root rot (*Fusarium oxysporum*) on greenhouse pepper in Ontario, Canada, *Can. J. Plant Pathol*., 2017, 39(2):121-132.

Crawford, R.F., The etiology and control of chile wilt, produced by *Fusarium annuum*, Agricultural Experiment Station of the New Mexico College of Agriculture and Mechanic Arts, State College, N.M., 1934, Bulletin No. 223, 20 pages.

Eshed, et al., Less-than-additive epistatic interactions of quantitative trait loci in tomato, *Genetics*, 1996, 143:1807-1817.

Juarez, J.A.A., et al., Regional study of phytopathogens associated to the pepper wilting in Guanajuato, Mexico, *Revista Mexicana de Ciencias Agricolas*, 2015, 11:2191-2197.

Kamburova, V.S., et al., Genome Editing in Plants: An Overview of Tools and Applications, *Intl J. of Agronomy*, 2017, Article ID 7315351, 15 pages.

Kraft, et al., Linkage disequilibrium and fingerprinting in sugar beet, *Theor. App. Genet*., 2000, 101:323-326.

Leonian, L.H., Fusarium wilt of chile pepper, New Mexico College of Agriculture and Mechanic Arts, Agricultural Experiment Station, State College, N.M., 1919, Bulletin No. 121, 32 pages.

(Continued)

*Primary Examiner* — Medina A Ibrahim

(74) *Attorney, Agent, or Firm* — Jondle & Associates, P.C.

(57) ABSTRACT

Methods for combining *fusarium* resistance and peppers and the *fusarium* resistant peppers produced by the method are disclosed. The invention relates to the plants and seeds of *fusarium* resistant pepper plants and to methods for producing a *fusarium* resistant pepper plant by crossing the *fusarium* resistant pepper plant with itself or another cultivar. The invention also relates to methods for producing locus conversion plants and genetically modified plants of *fusarium* resistant pepper plants and to the plants produced by those methods. This invention also relates to *fusarium* resistant pepper cultivars or breeding cultivars and plant parts derived from *fusarium* resistant pepper plants, to methods for producing other *fusarium* resistant pepper cultivars, lines or plant parts derived from *fusarium* resistant pepper plants and to the *fusarium* resistant pepper plants, varieties, and their parts derived from the use of those methods.

1 Claim, No Drawings

(56) References Cited

OTHER PUBLICATIONS

Lomas-Cano, T., et al., First report of *Fusarium oxysporum* on sweet pepper seedlings in Almeria, Spain, *Plant Disease APS Journals*, 2014, 98(10):1435.
Pary, M.A., et al., Comparative study of different fungi associated with fruit rot of chilli and screening of chilli germplasm against *Colletotrichum capsici, Intl. J. Agri. Crop Sci*., 2013, 5(7):723-730.
Perez-Hernandez, A., et al., Damping-off and root rot of pepper caused by *Fusarium oxysporum* in Almeria Province, Spain, *Plant Disease APS Journals*, 2014, 98(8):1159.
Poehlman, J.M. and Sleper, D.A., Methods in Plant Breeding, Breeding Field Crops, 4th Ed. (1995), Iowa State University Press, pp. 172-174.
Shafique, S., et al., Management of *Fusarium oxysporum* f.sp. *capsici* by leaf extract of *Eucalyptus citriodora, Pak. J. Bot*., 2015, 47(3):1177-1182.
Silvar, C., et al., Resistance in pepper plants induced by *Fusarium oxysporum* f.sp. *lycopersici* involves different defence-related genes, *Plant Biol* (*Stuttg*), 2009, 11(1):68-74.
Singh, J.K., et al., Screening of chilli cultivars against fusarium wilt of chilli (*Capsicum annuum* L.), *International Journal of Agricultural Science and Research*, 2017, 7(1):235-240.
Velarde-Felix, S., et al., Occurrence of *Fusarium oxysporum* causing wilt on pepper in Mexico, *Can. J. Plant Pathol*., 2018, 10 pages.
Wongpia, A. and Lomthaisong, K., Changes in the 2DE protein profiles of chilli pepper (*Capsicum annuum*) leaves in response to *Fusarium oxysporum* infection, *ScienceAsia*, 2010, 36:259-270.

* cited by examiner

METHOD OF COMBINING FUSARIUM RESISTANCE AND PEPPER

CROSS REFERENCE TO RELATED APPLICATIONS

This application claims the benefit of priority from U.S. provisional patent application Ser. No. 62/744,714 filed on Oct. 12, 2018, which is incorporated herein by reference in its entirety.

BACKGROUND OF THE INVENTION

The present invention relates to a method of combining *fusarium* resistance and pepper and to the *fusarium* resistant peppers produced by the method. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include improved flavor, higher seed yield, improved color, resistance to diseases and insects, tolerance to drought and heat, and better agronomic quality.

Peppers (genus *Capiscum*) are native to the Americas and comprise a genus of more than 30 species of flowering plants in the nightshade family Solanaceae, many of which are cultivated worldwide for their edible, often pungent fruits. The genus includes all the varied forms of fleshy-fruited peppers, including the mild bell peppers that are used for fresh consumption and the hot peppers, such as habanero and tabasco, which may be used in relishes, pickled, or ground into powder for use as spices. Other peppers are grown as ornamental plants, and some have been used as medicines.

*Capiscum* consists of five domesticated species: *C. annuum, C. baccatum, C. chinense, C. frutescens*, and *C. pubescens*. *C. annuum* is the most common and extensively cultivated of the domesticated species and comprises peppers having a wide variety of shapes and sizes, both mild and hot. For example, *C. annuum* includes the large, mild, bell pepper variety, which is sold in both its immature green state and its red, yellow, or orange ripe state. Also included in *C. annuum* are pepper varieties such as the Anaheim chile which is often used for stuffing, dried ancho (also known as poblano) chile which is used to make chili powder, the mild to hot jalapeño pepper, and smoked, ripe jalapeño, known as chipotle.

Peppers are very nutritious and are an excellent source of Vitamin C and Vitamin B6, although nutritional content is altered by the way they are prepared and consumed. Most peppers contain capsaicin, which produces the strong spicy or burning sensation often experienced by consumers. In addition to being used to provide added spice in food, capsaicin has numerous medical and pharmaceutical usages, as well as being an active ingredient in personal defense pepper sprays and used to deter pests.

Peppers grown in temperate regions are herbaceous annuals. However, where temperatures do not drop below freezing, peppers are herbaceous perennials. A pepper plant's growth habit may be prostrate, compact, or erect, but it is determinate in that after it produces nine to eleven leaves a single stem terminates in flowers. These plants are grown for the edible fleshy fruit produced by this dichotomous growth. Peppers are non-climacteric which means they do not produce ethylene. They need to stay on the vine to continue the ripening process. A deep taproot will form if the plant root system is uninjured during transplanting. The spindle root will develop fibrous secondary root systems spreading laterally and downward. On the soil surface the stem will produce adventitious roots, but not as easily as tomatoes. The leaves of the pepper plant arise singly and are simple, entire, and asymmetrical. Typical of all Solanaceous plants, the leaves are arranged alternately on the stem. They are shiny and glabrous and vary in shape from broadly ovate to ovate lanceolate. The flowers develop singly or in twos or threes continuously as the upper structure of the plant proliferates. The corolla is white and five lobed while the anthers are bluish or yellowish in color. The flowers have an open anther formation and will indefinitely self-pollinate. They are also pollinated by insects, which increases the chances of cross-pollination. Unlike tomatoes, whose pollen becomes nonviable in high temperatures, the pepper flower's pollen is not extremely heat sensitive and it remains viable up to 100° Fahrenheit producing fruit throughout the season.

The fruit of a pepper plant is classified as a berry with colors from green, yellow, red, purple, black, brown, white, and orange. Green is an immature fruit, yet commonly eaten this way, and as the fruit matures it changes color. In most commercial cultivars, color changes are from green to red, green to yellow, or green to orange. Usually, fruits of the purple and white varieties have these colors as they develop, and therefore do not have a green stage. For fruit to set, the ovaries need to be fertilized. Auxin is then produced by the seeds, which determine fruit cell elongation. The number of seeds fertilized will determine the size and shape of the fruit. The seeds develop on the interior and attach to the veins. Fully developed seeds are kidney shaped. There are about 4,500 seeds per ounce.

Diseases and insects can cause problems for pepper plant production in many areas. Excessive moisture from rain, saturated soils and high humidity plays a major role in the occurrence of both bacterial and fungal diseases. Some of these diseases include *Phytophthora* root rot (*Phythophthora capsici*), *Verticillium* wilt (*Verticillium dahliae* and *V. albo-atrum*), *Rhizoctonia* root rot (*Rhizoctonia solani*), bacterial leaf spot and soft rot, *Pythium* damping off and root rot, powdery mildew, anthracnose, and *Fusarium* wilt (*Fusarium* spp.).

Therefore, developing new and improved pepper plants having improved agronomical characteristics and resistance to diseases, is highly desirable.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there are provided novel pepper plants having *Fusarium oxysporum* resistance. The invention further relates to novel pepper plants having resistance to *Fusarium oxysporum* f. sp. *capsici*. This invention thus relates to the seeds of *F. oxysporum* f. sp. *capsici* resistant pepper plants, to the plants of *F. oxysporum* f. sp. *capsici* resistant pepper plants, and to methods for producing a *F. oxysporum* f. sp. *capsici* resistant pepper plant, to methods for producing *F. oxysporum* f. sp. *capsici* resistant pepper plants containing in their genetic material one or more transgenes, and to the transgenic *F. oxysporum* f. sp. *capsici* resistant pepper plants produced by that method. This invention also relates to methods for producing other *F. oxysporum* f. sp. *capsici* resistant pepper plants derived from the *F. oxysporum* f. sp. *capsici* resistant pepper plants of the invention and to the *F. oxysporum* f. sp. *capsici* resistant pepper cultivar derived by the use of those methods. This invention further relates to hybrid pepper seeds and plants produced by crossing a *F. oxysporum* f. sp. *capsici* isolate resistant pepper plant with another pepper variety.

In a further aspect, the invention provides for pepper plants that are resistant to infection by *Fusarium oxysporum* f. sp. *capsici* isolates belonging to *Fusarium oxysporum* species complex (FOSC) group, including but not limited to *F. oxysporum* f. sp. *capsici* isolates SLP F2-2, SLP F2-4, SLP F2-1, SLP F1-4 and SLP F1-2-(4). Prior to the current invention, *F. oxysporum* f. sp. *capsici* isolates SLP F2-2, SLP F2-4, SLP F2-1, SLP F1-4 and SLP F1-2-(4) were unknown, and there were no known pepper plants having resistance to *F. oxysporum* f. sp. *capsici* isolates SLP F2-2, SLP F2-4, SLP F2-1, SLP F1-4 and SLP F1-2-(4).

In another aspect, the present invention provides for methods of producing a *fusarium* resistant pepper plant, said method comprising:

a. Selecting diseased pepper plants and tissue samples;
b. Growing, isolating and purifying disease causing fungus from said selected plants into one or more fungal isolates;
c. Extracting DNA from said isolates and performing PCR;
d. Performing phylogenetic analyses on said DNA to characterize and identify the fungus;
e. Identifying a fungal isolate of *Fusarium oxysporum* f. sp. *capsici* as the disease causing fungus;
f. Performing pathogenicity tests on uninfected pepper plants using said fungal isolate;
g. Selecting pepper plants having resistance to said fungal isolate; and
h. Producing a *fusarium* resistant pepper plant wherein said plant is resistant to infection by said *F. oxysporum* f. sp. *capsici* isolate.

The invention further provides methods for developing additional *Fusarium oxysporum* f. sp. *capsici* resistant pepper plants in a pepper plant breeding program using plant breeding techniques including recurrent selection, backcrossing, pedigree breeding, restriction fragment length polymorphism enhanced selection, genetic marker enhanced selection, and transformation. Seeds, pepper plants, and parts thereof, produced by such breeding methods are also part of the invention, including inbred and hybrid *F. oxysporum* f. sp. *capsici* resistant pepper lines.

In another aspect, the invention relates to *F. oxysporum* f. sp. *capsici* resistant pepper plants, including but not limited to inbred pepper lines 3960, MXP021, and 3958. Also provided are pepper plants having the physiological and morphological characteristics of inbred pepper lines 3960, MXP021, and 3958. This invention thus relates to the seeds of inbred pepper lines 3960, MXP021, and 3958, to the plants of inbred pepper lines 3960, MXP021, and 3958, and to methods for producing a *F. oxysporum* f. sp. *capsici* resistant pepper plant produced by crossing inbred pepper lines 3960, MXP021, and 3958 with itself or another pepper plant, to methods for producing inbred pepper lines 3960, MXP021, and 3958 containing in its genetic material one or more transgenes, and to the transgenic *F. oxysporum* f. sp. *capsici* resistant pepper plants produced by that method. This invention also relates to methods for producing other pepper lines derived from inbred pepper lines 3960, MXP021, and 3958 and to the pepper lines derived by the use of those methods. This invention further relates to hybrid pepper seeds and plants produced by crossing inbred pepper lines 3960, MXP021, and 3958 with another pepper variety.

In another aspect, the present invention provides regenerable cells for use in tissue culture of *F. oxysporum* f. sp. *capsici* resistant pepper plants. In a further aspect, the present invention provides regenerable cells for use in tissue culture of *F. oxysporum* f. sp. *capsici* resistant pepper plants, including but not limited to inbred pepper pepper lines 3960, MXP021, and 3958. The tissue culture will preferably be capable of regenerating plants having essentially all of the physiological and morphological characteristics of the foregoing *fusarium* resistant pepper plant, and of regenerating plants having substantially the same genotype as the foregoing *F. oxysporum* f. sp. *capsici* resistant pepper plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, and seeds. Still further, the present invention provides *fusarium* resistant pepper plants regenerated from the tissue cultures of the invention.

In another aspect, the present invention provides *F. oxysporum* f. sp. *capsici* resistant pepper plants further comprising a single locus conversion. In a further aspect, the present invention provides for *F. oxysporum* f. sp. *capsici* resistant pepper plants comprising a single locus conversion, including but not limited to inbred pepper lines 3960, MXP021, and 3958. In one embodiment, the *F. oxysporum* f. sp. *capsici* resistant pepper plant is defined as comprising the single locus conversion and otherwise capable of expressing all of the morphological and physiological characteristics of the *F. oxysporum* f. sp. *capsici* resistant pepper or inbred pepper lines 3960, MXP021, and 3958. In particular embodiments of the invention, the single locus conversion may comprise a transgenic gene which has been introduced by genetic transformation into the *F. oxysporum* f. sp. *capsici* resistant pepper lines 3960, MXP021, and 3958 or a progenitor thereof. A transgenic or non-transgenic single locus conversion can also be introduced by backcrossing, as is well known in the art. In still other embodiments of the invention, the single locus conversion may comprise a dominant or recessive allele. The locus conversion may confer potentially any trait upon the single locus converted plant, including herbicide resistance, insect or pest resistance, resistance to bacterial, fungal, or viral disease, modified fatty acid metabolism, modified carbohydrate metabolism, male fertility or sterility, improved nutritional quality, and industrial usage.

The invention further relates to methods for genetically modifying a *F. oxysporum* f. sp. *capsici* resistant pepper plant, including but not limited to inbred pepper lines 3960, MXP021, and 3958, and to the modified pepper plant produced by those methods. The genetic modification methods may include, but are not limited to mutation, genome editing, RNA interference, gene silencing, backcross conversion, genetic transformation, single and multiple gene conversion, and/or direct gene transfer.

The *F. oxysporum* f. sp. *capsici* resistant pepper plants of this invention, including but not limited to inbred pepper lines 3960, MXP021, and 3958, may further comprise, or have, a cytoplasmic factor or other factor that is capable of conferring male sterility. Male sterility may also be provided by nuclear genes such as the recessive ms gene. Parts of the pepper plants of the present invention are also provided, such as pollen obtained from an inbred plant and an ovule of the inbred plant.

In a further aspect of the invention, the genetic complement of *F. oxysporum* f. sp. *capsici* resistant pepper plants, including but not limited to inbred pepper lines 3960, MXP021, and 3958, is provided. The phrase 'genetic complement' is used to refer to the aggregate of nucleotide sequences, the expression of which sequences defines the phenotype of a cell or tissue of that plant. A genetic complement thus represents the genetic makeup of a cell, tissue or plant, and a hybrid genetic complement represents the genetic make-up of a hybrid cell, tissue or plant. The invention thus provides *F. oxysporum* f. sp. *capsici* resistant pepper plants, including but not limited to inbred pepper lines 3960, MXP021, and 3958 plant cells that have a genetic complement in accordance with the *F. oxysporum* f. sp. *capsici* resistant pepper plants, including but not limited to inbred pepper lines 3960, MXP021, and 3958 plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that *F. oxysporum* f. sp. *capsici* resistant pepper plants, including but not limited to inbred pepper lines 3960, MXP021, and 3958, could be identified by any of the many well-known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858), and Single Nucleotide Polymorphisms (SNPs) (Wang et al., 1998).

In another aspect, the invention provides a method of determining the genotype of a plant of *F. oxysporum* f. sp. *capsici* resistant pepper plants, including but not limited to inbred pepper lines 3960, MXP021, and 3958, comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In another aspect, the invention provides one or more markers for *Fusarium oxysporum* resistance in pepper, including one or more markers for *Fusarium oxysporum* f. sp. *capsici* isolates belonging to *Fusarium oxysporum* species complex (FOSC) group, including but not limited to *F. oxysporum* f. sp. *capsici* isolates SLP F2-2, SLP F2-4, SLP F2-1, SLP F1-4 and SLP F1-2-(4). In another aspect, the invention provides for methods of developing such markers.

This invention further relates to the $F_1$ hybrid pepper plants and plant parts grown from the hybrid seed produced by crossing a *F. oxysporum* f. sp. *capsici* resistant pepper plant, including but not limited to inbred pepper lines 3960, MXP021, and 3958, to a second pepper plant. Still further included in the invention are the seeds of an $F_1$ hybrid plant produced with the *F. oxysporum* f. sp. *capsici* resistant pepper plant, including but not limited to inbred pepper lines 3960, MXP021, and 3958, as one parent, the second generation ($F_2$) hybrid pepper plant grown from the seed of the $F_1$ hybrid plant, and the seeds of the $F_2$ hybrid plant. Thus, any such methods using the *F. oxysporum* f. sp. *capsici* resistant pepper plants, including but not limited to inbred pepper lines 3960, MXP021, and 3958, are part of this invention: selfing, backcrosses, hybrid production, crosses to populations, and the like. All plants produced using *F. oxysporum* f. sp. *capsici* resistant pepper plants, including but not limited to inbred pepper lines 3960, MXP021, and 3958 as at least one parent are within the scope of this invention. Advantageously, the pepper cultivar could be used in crosses with other, different, pepper plants to produce first generation ($F_1$) pepper hybrid seeds and plants with superior characteristics.

This invention also relates to pepper lines or breeding cultivars and plant parts derived from *F. oxysporum* f. sp. *capsici* resistant pepper plants, including but not limited to inbred pepper lines 3960, MXP021, and 3958. Still yet another aspect of the invention is a method of producing a pepper plant derived from the *F. oxysporum* f. sp. *capsici* resistant pepper plants, including but not limited to inbred pepper lines 3960, MXP021, and 3958, the method comprising the steps of: (a) preparing a progeny plant derived from a *F. oxysporum* f. sp. *capsici* resistant pepper plant, including but not limited to inbred pepper lines 3960, MXP021, and 3958, by crossing a plant of the *F. oxysporum* f. sp. *capsici* resistant pepper plant, including but not limited to inbred pepper lines 3960, MXP021, and 3958 with a second pepper plant; and (b) crossing the progeny plant with itself or a second plant to produce a progeny plant of a subsequent generation which is derived from a plant of the *F. oxysporum* f. sp. *capsici* resistant pepper plants, including but not limited to inbred pepper lines 3960, MXP021, and 3958. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred pepper plant derived from the *F. oxysporum* f. sp. *capsici* resistant pepper plants, including but not limited to inbred pepper lines 3960, MXP021, and 3958. Also provided by the invention is a plant produced by this and the other methods of the invention.

In another embodiment of the invention, the method of producing a pepper plant derived from the *F. oxysporum* f. sp. *capsici* resistant pepper plants, including but not limited to inbred pepper lines 3960, MXP021, and 3958, further comprises: (a) crossing the *F. oxysporum* f. sp. *capsici* resistant pepper plant, including but not limited to inbred pepper lines 3960, MXP021, and 3958-derived pepper plant with itself or another pepper plant to yield additional *F. oxysporum* f. sp. *capsici* resistant pepper plant, including but not limited to inbred pepper lines 3960, MXP021, and 3958-derived progeny pepper seed; (b) growing the progeny pepper seed of step (a) under plant growth conditions to yield additional *F. oxysporum* f. sp. *capsici* resistant pepper plants, including but not limited to inbred pepper lines 3960, MXP021, and 3958-derived pepper plants; and (c) repeating the crossing and growing steps of (a) and (b) to generate further *F. oxysporum* f. sp. *capsici* resistant pepper plants, including but not limited to inbred pepper lines 3960, MXP021, and 3958-derived pepper plants. In specific embodiments, steps (a) and (b) may be repeated at least 1, 2, 3, 4, or 5 or more times as desired. The invention still further provides a pepper plant produced by this and the foregoing methods.

The invention further relates to a method of producing a commodity plant product from *F. oxysporum* f. sp. *capsici* resistant pepper plants, including but not limited to inbred pepper lines 3960, MXP021, and 3958, such as, but not limited to fresh pepper, cut, sliced, ground, pureed, dried, canned, jarred, washed, packaged, frozen and/or heated pepper, and to the commodity plant product produced by the method.

In addition to the exemplary aspects and embodiments described above, further aspects and embodiments will become apparent by reference by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Allele. The allele is any of one or more alternative forms of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Backcrossing. A process in which a breeder crosses progeny back to one of the parental genotypes one or more times. Commonly used to introduce one or more locus conversions from one genetic background into another (backcross conversion).

Cell. Cell as used herein includes a plant cell, whether isolated, in tissue culture or incorporated in a plant or plant part. The cell can be a cell, such as a somatic cell, of the variety having the same set of chromosomes as the cells of the deposited seed, or, if the cell contains a locus conversion or transgene, otherwise having the same or essentially the same set of chromosomes as the cells of the deposited seed.

CMS. Cytoplasmic male sterile.

Cotyledon. One of the first leaves of the embryo of a seed plant; typically one or more in monocotyledons, two in dicotyledons, and two or more in gymnosperms.

Crossing. The mating of two parent plants.

Cross-pollination. Fertilization by the union of two gametes from different plants.

Diploid. A cell or organism having two sets of chromosomes. The total number of chromosomes in diploid cells is described as 2n, which is twice the number of chromosomes in a haploid cell (n).

Diseased pepper plants. Refers to pepper plants afflicted by an apparent pepper wilt that results in leaf flagging and chlorosis, vascular discoloration of the root and crown, necrosis of leaflets and fruits that remain attached.

Emasculate. The removal of plant male sex organs or the inactivation of the organs with a cytoplasmic or nuclear genetic factor or a chemical agent conferring male sterility.

Essentially all the physiological and morphological characteristics. A plant having essentially all of the physiological and morphological characteristics of a designated plant has all of the characteristics of the plant that are otherwise present when compared in the same environment, other than an occasional variant trait that might arise during backcrossing, gene editing, or direct introduction of a transgene.

$F_{\#}$. The "F" symbol denotes the filial generation, and the # is the generation number, such as $F_1$, $F_2$, $F_3$, etc.

$F_1$ hybrid. The first generation progeny of the cross of two nonisogenic plants.

Fructose content. As used herein, "fructose content" means the quantity of fructose in a pepper fruit in mg/kg of fresh weight.

*Fusarium oxysporum* f. sp. *capsici*. *Fusarium oxysporum* is a pathogenic fungus common in soils around the word and the cause of *fusarium* wilt, a deadly vascular wilting syndrome in plants. *Fusarium oxysporum* comprises over 120 known strains or "special forms" (formae speciales; f. sp.), each of which is specific to a unique plant host in which it causes disease. *F. oxysporum* f. sp. *capsici* infects peppers plants, and isolates SLP F2-2, SLP F2-4, SLP F2-1, SLP F1-4 and SLP F1-2-(4) are previously unknown isolates identified by the inventors of the present invention and resulting in diseased pepper plants.

*Fusarium* resistant pepper plant(s) or lines. Refers to the *fusarium* resistant peppers of the present invention, wherein the pepper plants have resistance to infection by *Fusarium oxysporum* f. sp. *capsici*, including but not limited to isolates SLP F2-2, SLP F2-4, SLP F2-1, SLP F1-4 and SLP F1-2-(4). *Fusarium* resistant pepper plants of the present invention include, but are not limited to, inbred pepper lines 3960, MXP021, and 3958.

Gene. As used herein, "gene" refers to a segment of nucleic acid. A gene can be introduced into a genome of a species, whether from a different species or from the same species, using transformation or various breeding methods.

Glucose content. As used herein, "glucose content" means the quantity of glucose in a pepper fruit in mg/kg of fresh weight.

Gene converted (conversion). "Gene converted" or "Single gene converted" (or conversion) plant refers to plants which are developed by a plant breeding technique called backcrossing wherein essentially all of the desired morphological and physiological characteristics of an inbred are recovered in addition to the one or more genes transferred into the inbred via the backcrossing technique or via genetic engineering.

Gene silencing. The interruption or suppression of the expression of a gene at the level of transcription or translation.

Genetically modified. Describes an organism that has received genetic material from another organism, or had its genetic material modified, resulting in a change in one or more of its phenotypic characteristics. Methods used to modify, introduce or delete the genetic material may include mutation breeding, genome editing, RNA interference, gene silencing, backcross conversion, genetic transformation, single and multiple gene conversion, and/or direct gene transfer.

Genome editing. A type of genetic engineering in which DNA is inserted, replaced, modified or removed from a genome using artificially engineered nucleases or other targeted changes using homologous recombination. Examples include but are not limited to use of zinc finger nucleases (ZFNs), TAL effector nucleases (TALENs) and CRISPR/Cas9 or other CRISPR associated enzymes, such as Cpf1 or Cms1. (Ma et. al., *Molecular Plant,* 9:961-974 (2016); Belhaj et. al., *Current Opinion in Biotechnology,* 32:76-84 (2015); see also U.S. Pat. Nos. 8,697,359 and 9,896,696 and U.S. patent application Ser. No. 13/842,859).

Genotype. The genetic constitution of a cell or organism.

Haploid. A cell or organism having one set of the two sets of chromosomes in a diploid.

Internode. An "internode" means the stem segment between nodes.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A defined segment of DNA.

Locus conversion (also called a 'trait conversion'). A locus conversion refers to plants that have been modified in a manner that retains the overall genetics of the plant and further comprises one or more loci with a specific desired trait, such as male sterility, insect control, disease control or herbicide tolerance. Examples of single locus conversions include mutant genes, transgenes and native traits finely mapped to a single locus. One or more locus conversion traits may be introduced into a single plant.

Pathogenicity. Refers to the ability of an organism to cause disease, such as on a pepper plant.

Pathogenicity tests. Tests aimed at selecting the most virulent strain of the pathogen for the type of the target plant, such as pepper plant. Specimens of the target plant are grown and inoculated with strains of the candidate pathogen and pathogenicity is assessed from the symptoms exhibited by the plant.

Pedigree. Refers to the lineage or genealogical descent of a plant.

Pedigree breeding/selection. "Pedigree breeding" is a breeding method used during the inbreeding of populations of self- and cross-pollinated species for the development of desirable homogeneous lines. Pedigree selection generally begins with an $F_2$ population and continues until homogeneous lines are developed.

Pedigree distance. Relationship among generations based on their ancestral links as evidenced in pedigrees. May be measured by the distance of the pedigree from a given starting point in the ancestry.

Pepper or pepper fruit. As used herein, a "pepper" or "pepper fruit" is a fruit produced by a *Capsicum annuum* plant. The color of a pepper fruit can be green, red, yellow, orange, and, more rarely, white, black, and brown, depending on when they are harvested and the specific cultivar. Common pepper fruits include jalapeño, poblano, green pepper and chile.

Petiole. "Petiole" means the stalk of a leaf, attaching the leaf blade to the stem.

Phenotype. The detectable characteristics of a cell or organism, which characteristics are the manifestation of gene expression.

Phylogenetic analysis. The means of estimating the evolutionary relationships among species and classification of new species.

Plant. "Plant" includes plant cells, plant protoplasts, plant tissue, plant cells of tissue culture from which pepper plants can be regenerated, plant calli, plant clumps and plant cells that are intact in plants, or parts of plants such as pollen, flowers, seeds, leaves, stems and the like.

Plant part. Includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

Quantitative Trait Loci. "Quantitative Trait Loci" (QTL) refers to genetic loci that control to some degree, numerically representable traits that are usually continuously distributed.

Regeneration. "Regeneration" refers to the development of a plant from tissue culture.

RHS. "RHS" refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Self-pollination. The transfer of pollen from the anther to the stigma of the same plant.

Sib-cross. The cross of two plants having common parentage.

Single locus converted (conversion) plant. Plants which are developed by a plant breeding technique called backcrossing or via genetic engineering wherein essentially all of the morphological and physiological characteristics of a variety are recovered in addition to the desired trait or characteristics conferred by the single locus transferred into the variety via the backcrossing technique or via genetic engineering. A single locus may comprise one gene, or in the case of transgenic plants, one or more transgenes integrated into the host genome at a single site (locus).

Tissue culture. A composition comprising isolated cells of the same or a different type of collection of such cells organized into parts of a plant.

Transgene. A nucleic acid of interest that can be introduced into the genome of a plant by genetic engineering techniques (e.g., transformation) or breeding.

The following detailed description is of the currently contemplated modes of carrying out the invention. The description is not to be taken in a limiting sense, but is made merely for the purpose of illustrating the general principles of the invention, since the scope of the invention is best defined by the appended claims.

The present invention is directed to methods of producing *fusarium* resistant pepper plants (*Capsicum annuum*) and to the *fusarium* resistant pepper plants produced by the method, including but not limited to inbred pepper lines such as inbred pepper lines 3960, MXP021, and 3958. The pepper plants of the invention have been developed to be resistant to infection by the fungus *Fusarium oxysporum* f. sp. *capsici*, including but not limited to *Fusarium oxysporum* f. sp. *capsici* isolates SLP F2-2, SLP F2-4, SLP F2-1, SLP F1-4 and SLP F1-2-(4).

Inbred pepper line MXP021 is a poblano pepper line and 3960 and 3958 are jalapeño pepper lines all having resistance to *Fusarium oxysporum* f. sp. *capsici.*

Inbred pepper lines 3960, MXP021, and 3958 have shown uniformity and stability for the traits, within the limits of environmental influence for the traits. They have been self-pollinated a sufficient number of generations with careful attention to uniformity of plant type. The lines have been increased with continued observation for uniformity. No variant traits have been observed or are expected in pepper lines 3960, MXP021, and 3958.

Pepper line 3960 has the following morphological and physiological characteristics described (based on data primarily collected in Guamuchil):

TABLE 1

| VARIETY DESCRIPTION INFORMATION |
|---|
| General: |
| Type: Jalapeño |
| Usage: Fresh market |
| Type of culture: Traditional open field |
| Plant: |
| Shortened internode: None |
| Vigor: Average |
| Height: Medium size plant |
| Fruit: |
| Color before maturity: Green |
| Intensity of color before maturity: Medium light |
| Color at maturity: Red |
| Intensity of color at maturity: Medium |
| Capsaicin in placenta: Yes |
| Fruit length: 3.5 inches |
| Diameter: 1.25 inches to 1.4 inches |
| Predominant shape of longitudinal section: Conical |
| Predominant number of locules: 3 |
| Time of ripening (color change of fruits on 50% of plants): 90 days after planting |
| Disease and Pest Resistance: |
| *Fusarium oxysporum* f. sp. *capsici*: Resistant |
| Bacterial Spot (*Xanthomonas vesicatoria*): BS2 resistant |

Pepper line MXP021 has the following morphological and physiological characteristics described (based on data primarily collected in Guamuchil):

TABLE 2

| VARIETY DESCRIPTION INFORMATION |
|---|
| General: |
| Type: Poblano (Mulato) |
| Usage: Fresh/dry |
| Type of culture: Traditional open field |
| Plant: |
| Seedling (anthocyanin coloration of hypocotyl): None |
| Vigor: High |
| Height: Medium |
| Fruit: |
| Color before maturity: Green |
| Intensity of color before maturity: Dark |
| Color at maturity: Brown |
| Intensity of color at maturity: Medium |
| Capsaicin in placenta: Low |
| Fruit length: 17.0 cm |
| Diameter: 8.0 cm |
| Predominant shape of longitudinal section: Heart shaped |
| Predominant number of locules: 2 |
| Time of ripening (color change of fruits on 50% of plants): 95 days |
| Disease and Pest Resistance: |
| *Fusarium oxysporum* f. sp. *capsici*: Resistant |

Pepper line 3958 has the following morphological and physiological characteristics described (based on data primarily collected in Guamuchil):

TABLE 3

| VARIETY DESCRIPTION INFORMATION |
|---|
| General: |
| Type: Jalapeño |
| Usage: Fresh |
| Type of culture: Traditional open field |
| Plant: |
| Shortened internode: None |
| Vigor: Average |
| Height: Medium |
| Fruit: |
| Color before maturity: Green |
| Color at maturity: Red |
| Intensity of color at maturity: Medium |
| Capsaicin in placenta: Yes |
| Fruit length: 3.0 inches |
| Diameter: 1.25 inches |
| Predominant shape of longitudinal section: Conical |
| Predominant number of locules: 3 |
| Time of ripening (color change of fruits on 50% of plants): 90 days after planting |
| Disease and Pest Resistance: |
| *Fusarium oxysporum* f. sp. *capsici*: Resistant |
| Tobacco Etch Virus: Resistant |

The present invention is further directed to methods of producing *fusarium* resistant pepper plants, including but not limited to inbred pepper lines 3960, MXP021, and 3958 plants and seeds, and to the *fusarium* resistant pepper plants, including but not limited to inbred pepper lines 3960, MXP021, and 3958 plants and seeds produced by the method. Therefore, any methods using *fusarium* resistant pepper plants, including but not limited to inbred pepper lines 3960, MXP021, and 3958 are part of this invention: selfing, backcrosses, hybrid breeding, and crosses to populations.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Further Embodiments of the Invention

Pepper, and *Capsicum annuum* in general, is an important and valuable vegetable crop. Thus, a continuing goal of pepper plant breeders is to develop stable, high yielding pepper cultivars and hybrids that are agronomically sound and resistant to diseases. To accomplish this goal, the pepper breeder must select and develop pepper plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s)

being improved, and the type of cultivar used commercially (e.g., $F_1$ hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of pepper plant breeding is to develop new, unique, and superior pepper cultivars and hybrids. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same pepper traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior pepper cultivars.

The development of commercial pepper cultivars requires the development of pepper varieties, the crossing of these varieties and selection of superior hybrid crosses. The hybrid seed is produced by manual crosses between selected male-fertile parents or by using male sterility systems. These hybrids are selected for certain single gene traits such as fruit color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In a multiple-seed procedure, pepper breeders commonly harvest two or more seeds from each plant in a population and bulk them to form a bulk sample. Part of the bulk is used to plant the next generation and part is put in reserve. The procedure has been referred to as modified single-seed descent or the "pod-bulk" (for bean crops) technique.

The multiple-seed procedure has been used to save labor at harvest. It is considerably faster to extract seeds with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Mutation breeding is another method of introducing new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.,* 77:889-892 (1989).

Descriptions of other breeding methods that are commonly used for different traits and crops can be found in one of several reference books (e.g., Allard, "Principles of plant breeding," John Wiley & Sons, NY, University of California, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses," 2d Ed., Manograph 16:249, 1987; Fehr, "Principles of cultivar development," Theory and Technique (Vol 1) and Crop Species Soybean (Vol 2), Iowa State Univ., Macmillian Pub. Co., NY, 360-376, 1987; Poehlman and Sleper, "Breeding Field Crops" Iowa State University Press, Ames, 1995; Sprague and Dudley, eds., Corn and Improvement, 5th ed., 2006).

Genotypic Profile of *Fusarium* Resistant Peppers and Progeny

In addition to phenotypic observations, a plant can also be identified by its genotype. The genotype of a plant can be characterized through a genetic marker profile which can identify plants of the same variety or a related variety, or which can be used to determine or validate a pedigree. Genetic marker profiles can be obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, single nucleotide polymorphisms (SNPs), or genome-wide evaluations such as genotyping-by-sequencing (GBS). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety. Favorable genotypes and or marker profiles, optionally associated with a trait of interest, may be identified by one or more methodologies.

In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) *Nat Biotech* 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) *Nat Rev Genet* 11:31-46; and, Egan et al. (2012) *Am J Bot* 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) *PLoS ONE* 6:e19379), and expression methods. In some examples, no reference genome sequence is needed in order to complete the analysis.

The invention further provides a method of determining the genotype of a *Fusarium oxysporum* f. sp. *capsici* resistant pepper plant, including but not limited to inbred pepper lines 3960, MXP021, and 3958, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of *F. oxysporum* f. sp. *capsici* resistant pepper plant, including but not limited to pepper plants 3960, MXP021, and 3958.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

In some examples, a plant, a plant part, or a seed of *F. oxysporum* f. sp. *capsici* resistant pepper plant, including but not limited to pepper lines 3960, MXP021, and 3958 may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.,* 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. This technique may commonly be referred to as marker assisted selection. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Introduction of a New Trait or Locus into *Fusarium* Resistant Peppers

*F. oxysporum* f. sp. *capsici* resistant peppers, including but not limited to pepper lines 3960, MXP021, and 3958, represent a new base genetic variety into which a new locus or trait may be introgressed. Backcrossing and direct transformation represent two important methods that can be used to accomplish such an introgression.

Single Locus Conversions

When the term "pepper plant" is used in the context of the present invention, this also includes any single locus conversions of that variety. The term "single locus converted plant" or "single gene converted plant" refers to those pepper plants which are developed by backcrossing or genetic engineering, wherein essentially all of the desired morphological and physiological characteristics of a variety are recovered in addition to the one or more genes transferred into the variety via the backcrossing technique or genetic engineering. Backcrossing methods can be used with the present invention to improve or introduce a characteristic into the variety.

A backcross conversion of *F. oxysporum* f. sp. *capsici* resistant pepper plants, including but not limited to pepper lines 3960, MXP021, and 3958, occurs when DNA sequences are introduced through backcrossing (Hallauer, et al., "Corn Breeding," *Corn and Corn Improvements*, No. 18, pp. 463-481 (1988)), with *fusarium* resistant pepper plants, including but not limited to pepper lines 3960, MXP021, and 3958 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety.

A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in *F. oxysporum* f. sp. *capsici* resistant pepper plants, including but not limited to pepper lines 3960, MXP021, and 3958, comprises crossing *fusarium* resistant pepper plants, including but not limited to pepper lines 3960, MXP021, and 3958, grown from *F. oxysporum* f. sp. *capsici* resistant pepper plants, including but not limited to pepper lines 3960, MXP021, and 3958 seed with plants of another pepper variety that comprise the desired trait or locus, selecting $F_1$ progeny plants that comprise the desired trait or locus to produce selected $F_1$ progeny plants, crossing the selected progeny plants with the *F. oxysporum* f. sp. *capsici* resistant pepper plants, including but not limited to pepper lines 3960, MXP021, and 3958 plants to produce backcross progeny plants, selecting for backcross progeny plants that have the desired trait or locus and the morphological characteristics of *F. oxysporum* f. sp. *capsici* resistant pepper plants, including but not limited to pepper lines 3960, MXP021, and 3958 to produce selected backcross progeny plants, and backcrossing to *F. oxysporum* f. sp. *capsici* resistant pepper plants, including but not limited to pepper lines 3960, MXP021, and 3958 three or more times in succession to produce selected fourth or higher backcross progeny plants that comprise said trait or locus. The modified *F. oxysporum* f. sp. *capsici* resistant pepper plants, including but not limited to pepper lines 3960, MXP021, and 3958 may be further characterized as having the physiological and morphological characteristics of *F. oxysporum* f. sp. *capsici* resistant pepper plants, including but not limited to pepper lines 3960, MXP021, and 3958 listed in Tables 1-3 as determined at the 5% significance level when grown in the same environmental conditions and/or may be characterized by percent similarity or identity to *F. oxysporum* f. sp. *capsici* resistant pepper plants, including but not limited to pepper lines 3960, MXP021, and 3958 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny pepper seed by adding a step at the end of the process that comprises crossing *fusarium* resistant pepper plants, including but not limited to pepper lines 3960, MXP021, and 3958 with the introgressed trait or locus with a different pepper plant and harvesting the resultant first generation progeny pepper seed.

Methods for Genetic Engineering of Pepper

With the advent of molecular biological techniques that have allowed the isolation and characterization of genes that encode specific protein products, scientists in the field of plant biology developed a strong interest in engineering the genome of plants (genetic engineering) to contain and express foreign genes, or additional, or modified versions of native, or endogenous, genes (perhaps driven by different promoters) in order to alter the traits of a plant in a specific manner. Plants altered by genetic engineering are often referred to as 'genetically modified'. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Vectors used for the transformation of pepper cells are not limited so long as the vector can express an inserted DNA in the cells. For example, vectors comprising promoters for constitutive gene expression in pepper cells (e.g., cauliflower mosaic virus 35S promoter) and promoters inducible by exogenous stimuli can be used. Examples of suitable vectors include pBI binary vector. The "pepper cell" into which the vector is to be introduced includes various forms of pepper cells, such as cultured cell suspensions, protoplasts, leaf sections, and callus. A vector can be introduced into pepper cells by known methods, such as the polyethylene glycol method, polycation method, electroporation, *Agrobacterium*-mediated transfer, particle bombardment and direct DNA uptake by protoplasts. See, e.g., Pang et al. (The Plant J., 9, 899-909, 1996).

Methods for Pepper Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science,* 227:1229 (1985); Curtis, et al., *Journal of Experimental Botany,* 45:279, 1441-1449 (1994); Tones, et al., *Plant Cell Tissue and Organ Culture,* 34:3, 279-285 (1993); and Dinant, et al., *Molecular Breeding,* 3:1, 75-86 (1997). *A.*

*tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method for delivering transforming DNA segments to plant cells is microprojectile-mediated transformation, or microprojectile bombardment. In this method, particles are coated with nucleic acids and delivered into cells by a propelling force. Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol Plant*, 7:206 (1990); Klein, et al., *Bio/technology*, 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985) and Christou, et al., *PNAS*, 84:3962 (1987). Direct uptake of DNA into protoplasts using $CaCl_2$ precipitation, calcium phosphate precipitation, polyethylene glycol treatment, polyvinyl alcohol, or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Saker, M., Kuhne, T., *Biologia Plantarum*, 40(4):507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Electroporation of protoplasts and whole cells and tissues has also been described. Donn, et al., In Abstracts of VIIth International Congress on Plant Cell and Tissue Culture IAPTC, A2-38, p. 53, 1990; D'Halluin, et al., *Plant Cell*, 4:1495-1505, 1992; and Spencer, et al., *Plant Mol. Biol.*, 24:51-61, 1994. Another illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pepper cells.

Transformation of plants and expression of foreign genetic elements is exemplified in Choi et al., *Plant Cell Rep.*, 13: 344-348, 1994 and Ellul et al., *Theor. Appl. Genet.*, 107:462-469, 2003.

Following transformation of pepper target tissues, expression of selectable marker genes allows for preferential selection of transformed cells, tissues and/or plants, using regeneration and selection methods now well known in the art.

The methods described herein for transformation would typically be used for producing a transgenic variety. The transgenic variety could then be crossed, with another (non-transformed or transformed) variety, in order to produce a new transgenic variety. Alternatively, a genetic trait which has been engineered into a particular pepper cultivar using the transformation techniques described could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Expression Vectors for Pepper Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.,* 5:387 (1987); Teeri, et al., *EMBO J.,* 8:343 (1989); Koncz, et al., *PNAS,* 84:131 (1987); and DeBlock, et al., *EMBO J.,* 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.,* 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science,* 263:802 (1994). GFP and mutants of GFP may be used as screenable markers.

Expression Vectors for Pepper Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in pepper. Optionally, the inducible promoter is operably linked to a nucleotide sequence encoding a signal sequence which is operably linked to a gene for expression in pepper. With an inducible promoter, the rate of transcription increases in response to an inducing agent.

Any inducible promoter can be used in the instant invention. See Ward, et al., *Plant Mol. Biol.,* 22:361-366 (1993). Exemplary inducible promoters include, but are not limited to, that from the ACEI system which responds to copper (Meft, et al., *PNAS,* 90:4567-4571 (1993)); In2 gene from maize which responds to benzenesulfonamide herbicide safeners (Hershey, et al., *Mol. Gen. Genet.,* 227:229-237 (1991) and Gatz, et al., *Mol. Gen. Genet.,* 243:32-38 (1994)) or Tet repressor from Tn10 (Gatz, et al., *Mol. Gen. Genet.,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS,* 88:0421 (1991).

B. Constitutive Promoters:

A constitutive promoter is operably linked to a gene for expression in pepper or the constitutive promoter is operably linked to a nucleotide sequence encoding a signal sequence which is operably linked to a gene for expression in pepper.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT Application No. WO 96/30530.

C. Tissue-Specific or Tissue-Preferred Promoters:

A tissue-specific promoter is operably linked to a gene for expression in pepper. Optionally, the tissue-specific promoter is operably linked to a nucleotide sequence encoding a signal sequence which is operably linked to a gene for expression in pepper. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Additional Methods for Genetic Engineering of Pepper

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As a non-limiting example, a genetically modified plant variety is generated using "custom" or engineered endonucleases such as meganucleases produced to modify plant genomes (see e.g., WO 2009/114321; Gao et al. (2010) *Plant Journal* 1:176-187). Another site-directed engineering method is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Site-specific modification of plant genomes can also be performed using the bacterial type II CRISPR (clustered regularly interspaced short palindromic repeats)/Cas (CRISPR-associated) system, or other CRISPR-associated systems and methods, such as type III CRISPR, those using the nucleases Cpf1 or Cms1 or Csm, or similar systems and methods. See e.g., Belhaj et al., (2013), *Plant Methods* 9: 39; The Cas9/guide RNA-based system allows targeted cleavage of genomic DNA guided by a customizable small noncoding RNA in plants (see e.g., WO 2015026883A1 and U.S. Pat. Nos. 8,697,359 and 9,896,696 and U.S. patent application Ser. No. 13/842,859 incorporated herein by reference).

A genetic map can be generated that identifies the approximate chromosomal location of an integrated DNA molecule, for example via conventional restriction fragment length polymorphisms (RFLP), polymerase chain reaction (PCR) analysis, simple sequence repeats (SSR), and single nucleotide polymorphisms (SNP). For exemplary methodologies in this regard, see Glick and Thompson, *Methods in Plant Molecular Biology and Biotechnology*, pp. 269-284 (CRC Press, Boca Raton, 1993).

Wang et al. discuss "Large Scale Identification, Mapping and Genotyping of Single-Nucleotide Polymorphisms in the Human Genome", *Science* (1998) 280:1077-1082, and similar capabilities are increasingly available for the pepper genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons could involve hybridizations, RFLP, PCR, SSR, sequencing or combinations thereof, all of which are conventional techniques. SNPs may also be used alone or in combination with other techniques.

*Fusarium* Resistant Peppers Further Comprising a Transgene

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into *F. oxysporum* f. sp. *capsici* resistant peppers, including but not limited to pepper lines 3960, MXP021, and 3958. Transgenic variants of *F. oxysporum* f. sp. *capsici* resistant peppers, including but not limited to pepper lines 3960, MXP021, and 3958 plants, seeds, cells, and parts thereof or derived therefrom are provided. Transgenic variants of *F. oxysporum* f. sp. *capsici* resistant pepper plants, including but not limited to pepper lines 3960, MXP021, and 3958 comprise the physiological and morphological characteristics of *F. oxysporum* f. sp. *capsici* resistant peppers, including but not limited to pepper lines 3960, MXP021, and 3958, such as listed in Tables 1-3 as determined at the 5% significance level when grown in the same environmental conditions, and/or may be characterized or identified by percent similarity or identity to *F. oxysporum* f. sp. *capsici* resistant peppers, including but not limited to pepper lines 3960, MXP021, and 3958 as determined by SSR or other molecular markers.

In some examples, transgenic variants of *F. oxysporum* f. sp. *capsici* resistant peppers, including but not limited to pepper lines 3960, MXP021, and 3958 are produced by introducing at least one transgene of interest into *F. oxysporum* f. sp. *capsici* resistant peppers, including but not limited to pepper lines 3960, MXP021, and 3958 by transforming *F. oxysporum* f. sp. *capsici* resistant peppers, including but not limited to pepper lines 3960, MXP021, and 3958 with a polynucleotide comprising the transgene of interest. In other examples, transgenic variants of *F. oxysporum* f. sp. *capsici* resistant peppers, including but not limited to pepper lines 3960, MXP021, and 3958 are produced by introducing at least one transgene by introgressing the transgene into *F. oxysporum* f. sp. *capsici* resistant peppers, including but not limited to pepper lines 3960, MXP021, and 3958 by crossing.

In one example, a process for modifying *F. oxysporum* f. sp. *capsici* resistant peppers, including but not limited to pepper lines 3960, MXP021, and 3958 with the addition of a desired trait, said process comprising transforming a pepper plant of *F. oxysporum* f. sp. *capsici* resistant peppers, including but not limited to pepper lines 3960, MXP021, and 3958 with a transgene that confers a desired trait is provided. Therefore, transgenic *F. oxysporum* f. sp. *capsici* resistant peppers, including but not limited to pepper lines 3960, MXP021, and 3958 cells, plants, plant parts, and seeds produced from this process are provided. In some examples one more desired traits may include traits such as sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. The specific gene may be any known in the art or listed herein, including but not limited to a polynucleotide conferring resistance to an ALS-inhibitor herbicide, imidazolinone, sulfonylurea, protoporphyrinogen oxidase (PPO) inhibitors, hydroxyphenyl pyruvate dioxygenase (HPPD) inhibitors, glyphosate, glufosinate, triazine, 2,4-dichlorophenoxyacetic acid (2,4-D), dicamba, broxynil, metribuzin, or benzonitrile herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to bacterial leaf spot (*Xanthomonas*), bacterial soft rot, black spot, *Rhizoctonia, Pythium* spp., *Phytophthora capsici, Fusarium oxysporum*, powdery mildew, southern blight, mosaic viruses, tomato spotted wilt virus, anthracnose, or other plant pathogens.

Foreign Protein Genes and Agronomic Genes

By means of the present invention, plants can be genetically engineered to express various phenotypes of agronomic interest. Through the transformation of pepper, the expression of genes can be altered to enhance disease resistance, insect resistance, herbicide resistance, agronomic, nutritional quality, and other traits. Transformation can also be used to insert DNA sequences which control or help control male-sterility. DNA sequences native to pepper, as well as non-native DNA sequences, can be transformed into pepper and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, Curr. *Op. Plant Bio.,* 2:109-113 (1999)); target-RNA-specific ribozymes (Haseloff, et al., *Nature,* 334: 585-591 (1988)); hairpin structures (Smith, et al., *Nature,* 407:319-320 (2000); WO 99/53050; WO 98/53083); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary nucleotide sequences and/or native loci that confer at least one trait of interest, which optionally may be conferred or altered by genetic engineering, transformation or introgression of a transformed event include, but are not limited to, those categorized below:

A. Genes that Confer Resistance to Pests or Disease and that Encode:

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., *Gene,* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., *Plant Mol. Biol.,* 24:25 (1994), who disclose the nucleotide sequences of several *Clivia miniata* mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., *J. Biol. Chem.,* 262:16793 (1987) (nucleotide sequence of rice cysteine proteinase inhibitor); Huub, et al., *Plant Mol. Biol.,* 21:985 (1993) (nucleotide sequence of cDNA encoding tobacco proteinase inhibitor I); and Sumitani, et al., *Biosci. Biotech. Biochem.,* 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

6. An insect-specific hormone or pheromone, such as an ecdysteroid and juvenile hormone, a variant thereof, a mimetic based thereon, or an antagonist or agonist thereof. See, for example, the disclosure by Hammock, et al., *Nature,* 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, *J. Biol. Chem.,* 269:9 (1994) (expression cloning yields DNA coding for insect diuretic hormone receptor); Pratt, et al., *Biochem. Biophys. Res. Comm.,* 163:1243 (1989) (an allostatin is identified in *Diploptera puntata*); Chattopadhyay, et al., *Critical Reviews in Microbiology,* 30(1):33-54 (2004); Zjawiony, *J Nat Prod,* 67(2):300-310 (2004); Carlini & Grossi-de-Sa, *Toxicon,* 40(11):1515-1539 (2002); Ussuf, et al., *Curr Sci.,* 80(7):

847-853 (2001); Vasconcelos & Oliveira, *Toxicon,* 44(4): 385-403 (2004). See also, U.S. Pat. No. 5,266,317 to Tomalski, et al., which discloses genes encoding insect-specific, paralytic neurotoxins.

8. An insect-specific venom produced in nature, by a snake, a wasp, etc. For example, see Pang, et al., *Gene,* 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.,* 23:691 (1993), who teach the nucleotide sequence of a cDNA encoding tobacco hornworm chitinase, and Kawalleck, et al., *Plant Mol. Biol.,* 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.,* 24:757 (1994), of nucleotide sequences for mung bean calmodulin cDNA clones, and Griess, et al., *Plant Physiol.,* 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.,* 89:43 (1993), of heterologous expression of a cecropin-β, lytic peptide analog to render transgenic tobacco plants resistant to *Pseudomonas solanacearum.*

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.,* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific or pathogen protein specific antibody. See, for example, Safarnejad, et al. (2011) Biotechnology Advances 29(6): 961-971, reviewing antibody-mediated resistance against plant pathogens.

17. A developmental-arrestive protein produced in nature by a pathogen or a parasite. Thus, fungal endo-α-1,4-D-polygalacturonases facilitate fungal colonization and plant nutrient released by solubilizing plant cell wall homo-α-1,4-D-galacturonase. See Lamb, et al., *Bio/technology,* 10:1436 (1992). The cloning and characterization of a gene which encodes a bean endopolygalacturonase-inhibiting protein is described by Toubart, et al., *Plant J.,* 2:367 (1992).

18. A developmental-arrestive protein produced in nature by a plant. For example, Logemann, et al., *Bio/technology,* 10:305 (1992), have shown that transgenic plants expressing the barley ribosome-inactivating gene have an increased resistance to fungal disease.

19. Genes involved in the Systemic Acquired Resistance (SAR) Response and/or the pathogenesis-related genes. See Fu et al. (2013) Annu Rev Plant Biol. 64:839-863, Luna et al. (2012) Plant Physiol. 158:844-853, Pieterse & Van Loon (2004) Curr Opin Plant Bio 7:456-64; and Somssich (2003) Cell 113:815-816.

20. Antifungal genes. See, Ceasar et al. (2012) Biotechnol Lett 34:995-1002; Bushnell et al. (1998) Can J Plant Path 20:137-149. Also, see US Patent Application Publications US2002/0166141; US2007/0274972; US2007/0192899; US2008/0022426; and U.S. Pat. Nos. 6,891,085; 7,306,946; and 7,598,346.

21. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

22. Detoxification genes, such as for fumonisin, beauvericin, moniliformin, and zearalenone and their structurally-related derivatives. For example, see Schweiger et al. (2013) Mol Plant Microbe Interact. 26:781-792 and U.S. Pat. Nos. 5,716,820; 5,792,931; 5,798,255; 5,846,812; 6,083,736; 6,538,177; 6,388,171; and 6,812,380.

23. Cystatin and cysteine proteinase inhibitors. See, for example, Popovic et al. (2013) Phytochemistry 94:53-59. van der Linde et al. (2012) Plant Cell 24:1285-1300 and U.S. Pat. No. 7,205,453.

24. Defensin genes. See, for example, De Coninck et al. (2013) Fungal Biology Reviews 26: 109-120, International Patent Publication WO03/000863 and U.S. Pat. Nos. 6,911,577; 6,855,865; 6,777,592; and 7,238,781.

Any of the above listed disease or pest resistance genes (1-24) can be introduced into the claimed pepper cultivar through a variety of means including but not limited to transformation and crossing.

B. Genes that Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO J.,* 7:1241 (1988) and Miki, et al., *Theor. Appl. Genet.,* 80:449 (1990), respectively. See also, U.S. Pat. Nos. 5,084,082; 5,605,011; 5,013,659; 5,141,870; 5,767,361; 5,731,180; 5,304,732; 4,761,373; 5,331,107; 5,928,937; and 5,378,824; US2007/0214515; US2013/0254944; and WO96/33270.

2. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT), dicamba and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. In addition, glyphosate resistance can be imparted to plants by the over expression of genes encoding glyphosate N-acetyltransferase. See, for example, US2004/0082770; US2005/0246798; and US2008/0234130 which are incorporated herein by reference for this purpose. A DNA molecule encoding a mutant aroA gene can be obtained under ATCC Accession No. 39256, and the nucleotide sequence of the mutant gene is disclosed in U.S. Pat. No. 4,769,061 to Comai. See also, Umaballava-Mobapathie in *Transgenic Research,* 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology,* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Accl-S1, Accl-S2, and Accl-S3 genes described by Marshall, et al., *Theor. Appl. Genet.,* 83:435 (1992). For other polynucleotides and/or methods or uses see also U.S. Pat. Nos. 6,566,587; 6,338,961; 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; 7,608,761; 7,632,985; 8,053,184; 6,376,754; 7,407,913; and 5,491,288; EP1173580; WO01/66704; EP1173581; US2012/0070839; US2005/0223425; US2007/0197947; US2010/0100980; US2011/0067134; and EP1173582, which are incorporated herein by reference for this purpose.

3. An herbicide that inhibits photosynthesis, such as a triazine (psbA and gs+ genes) and a benzonitrile (nitrilase gene). Przibilla, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992). The herbicide methyl viologen inhibits CO.sub.2 assimilation. Foyer et al. (Plant Physiol., 109:1047-1057, 1995) describe a plant overexpressing glutathione reductase (GR) which is resistant to methyl viologen treatment.

4. Acetohydroxy acid synthase, which has been found to make plants that express this enzyme resistant to multiple types of herbicides, has been introduced into a variety of plants. See Hattori, et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.,* 106:17 (1994)), genes for glutathione reductase and superoxide dismutase (Aono, et al., *Plant Cell Physiol.,* 36:1687 (1995)), and genes for various phosphotransferases (Datta, et al., *Plant Mol. Biol.,* 20:619 (1992)).

5. Protoporphyrinogen oxidase (PPO; protox) is the target of the PPO-inhibitor class of herbicides; a PPO-inhibitor resistant PPO gene was recently identified in *Amaranthus tuberculatus* (Patzoldt et al., PNAS, 103(33):12329-2334, 2006). PPO is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

6. Genes that confer resistance to auxin or synthetic auxin herbicides. For example an aryloxyalkanoate dioxygenase (AAD) gene may confer resistance to arlyoxyalkanoate herbicides, such as 2,4-D, as well as pyridyloxyacetate herbicides, such as described in U.S. Pat. No. 8,283,522, and US2013/0035233. In other examples, a dicamba monooxygenase (DMO) is used to confer resistance to dicamba. Other polynucleotides of interest related to auxin herbicides and/or uses thereof include, for example, the descriptions found in U.S. Pat. Nos. 8,119,380; 7,812,224; 7,884,262; 7,855,326; 7,939,721; 7,105,724; 7,022,896; 8,207,092; US2011/067134; and US2010/0279866.

Any of the above listed herbicide genes (1-6) can be introduced into the claimed pepper cultivar through a variety of means including, but not limited to, transformation and crossing.

C. Genes that Confer or Contribute to a Value-Added Trait, such as:

1. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

2. Decreased phytate content—1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. See Raboy et al., *Maydica* 35:383 (1990).

3. Increased sweetness of the pepper by introducing a gene coding for monellin that elicits a flavor 100,000 times sweeter than sugar on a molar basis. See Penarrubia, et al., *Bio/technology,* 10:561-564 (1992).

4. Modified fatty acid metabolism, for example, by introducing into a plant an antisense gene of stearyl-ACP desaturase to increase stearic acid content of the plant. See Knultzon, et al., *PNAS,* 89:2625 (1992).

5. Modified carbohydrate composition effected, for example, by introducing into plants a gene coding for an enzyme that alters the branching pattern of starch. See Shiroza, et al., *J. Bacteriol.,* 170:810 (1988) (nucleotide sequence of *Streptococcus mutants* fructosyltransferase gene); Steinmetz, et al., *Mol. Gen. Genet.,* 20:220 (1985) (nucleotide sequence of *Bacillus subtilis* levansucrase gene); Pen, et al., *Bio/technology,* 10:292 (1992) (production of transgenic plants that express *Bacillus lichenifonnis* α-amylase); Elliot, et al., *Plant Mol. Biol.,* 21:515 (1993) (nucleotide sequences of tomato invertase genes); Søgaard, et al., *J. Biol. Chem.,* 268:22480 (1993) (site-directed mutagenesis of barley α-amylase gene); and Fisher, et al., *Plant Physiol.,* 102:1045 (1993) (maize endosperm starch branching enzyme II).

6. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

D. Genes that Control Male-Sterility:

1. Introduction of a deacetylase gene under the control of a tapetum-specific promoter and with the application of the chemical N-Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.,* 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

E. Genes that Affect Abiotic Stress Resistance:

Genes that affect abiotic stress resistance (including but not limited to flowering, seed development, enhancement of nitrogen utilization efficiency, altered nitrogen responsiveness, drought resistance or tolerance, cold resistance or tolerance, high or low light intensity, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), U.S. Pat. No. 6,713,663 (FT), U.S. Pat. Nos. 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Tissue Culture

Further reproduction of the variety can occur by tissue culture and regeneration. Tissue culture of various tissues of pepper and regeneration of plants therefrom is well known and widely published. For example, reference may be had to Kim, et al., *J. Plant Biology,* 45(3):177-181 (2002); Teng, et al., *HortScience,* 27:9, 1030-1032 (1992); Teng, et al., *HortScience,* 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a very high rate of success. Thus, another aspect of this invention is to provide cells which upon growth and differentiation produce pepper plants having the physiological and morphological characteristics of *fusarium* resistant pepper plants, including but not limited to pepper lines 3960, MXP021, and 3958.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

As used herein, the term "plant" includes plant cells, plant protoplasts, plant cell tissue cultures from which pepper plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

EXAMPLES

In June 2015, pepper fields were found to be afflicted by an apparent wilt that resulted in leaf flagging and chlorosis, vascular discoloration of the root and crown, necrosis of leaflets and fruits that remain attached. The causal agent for the diseased peppers was unknown, therefore, studies were performed to isolate and identify the pathogen.

Example 1

Isolation and Purification of the Causal Agent

Roots of pepper plants showing wilting symptom were collected from fields in Mexico and were brought into the lab and washed thoroughly to remove any soil. The infected portion of the root tissues were surface disinfested with 0.5% sodium hypochlorite for 3 min and followed by a 3 min rinse with sterilized distilled water. Roots were dried in a laminar flow hood, sliced into ~1 mm cross-sections and plated on potato dextrose agar medium (PDA). Plates were incubated at room temperature (23±2° C.). Fungal spores were then streaked onto a new PDA plate and a single-spore colony was further transferred onto a new PDA plate. In total, five isolates were isolated and purified in this process.

Example 2

Phylogenetic Analysis to Identify and Characterize *Fusarium* Species

*Fusarium* isolates can only be grouped up to *Fusarium oxysporum* species complex level based on their nuclear gene sequences. Two 3-mm-diameter *Fusarium* species plugs from an actively growing fungal colony on PDA were transferred to 50 ml potato dextrose broth (PDB) and grown for 7 to 10 days on laboratory benches at room temperature (23+2° C.). Mycelium was harvested, and the genomic DNA was extracted. Extracted genomic DNA from these *Fusarium* isolates were used to generate partial sequences of the RNA polymerase II gene using RPB1 and RPB2 primer sets. Five *Fusarium* isolates' [isolates F2-2, F2-4, F2-1, F1-4 and F1-2-(4)] nuclear genes sequences were compared with other previously well characterized *Fusarium* species sequences deposited at the GeneBank of NCBI. Based on these nuclear gene sequences, these *Fusarium* isolates from pepper from Mexico belonged to *Fusarium oxysporum* species complex (FOSC) group.

Example 3

Host Range Study of *Fusarium Oxysporum* Species Complex Isolates from Pepper To identify *Fusarium oxysporum* isolates up to the forma specialis (f. sp.) level, the inventors performed its host range study on pepper and tomato and characterized symptoms (wilting vs rotting) development on these host plants. Thus, the virulence of these *Fusarium oxysporum* isolates was further characterized by inoculating them on pepper lines: CM334 and Jupiter, and tomato lines: Ohio 89-1 (R-check) and Hayslip (S-check). The results showed that *Fusarium oxysporum* isolates collected from pepper were pathogenic to pepper only but these were non-pathogenic to tomato. Similarly, *Fusarium oxysporum* f. sp. *radicis-lycopersici* isolate (TM HE0616) was only pathogenic on susceptible line Hayslip; however, it was non-pathogenic on pepper lines: CM334 and Jupiter. It was concluded that these *Fusarium oxysporum* isolates collected from pepper in Mexico were *Fusarium oxysporum* f. sp. *capsici*, as described previously (Perez-Hernandez et. al. (2014) *Plant Disease,* 98(8)1159). The sequences obtained from the isolates is evidence for the identification at the species level, and the pathogenicity on pepper and tomato provides evidence to identify these isolates at the forma specialis level.

Example 4

Pathogenicity Tests to Evaluate Pepper Lines Against *Fusarium Oxysporum* Species Complex Isolate Collected from Pepper Two *Fusarium oxysporum* f. sp. *capsici* isolates were pathogenic on pepper plants; however, one of the isolate SLP F1-2-(4) produced less amount of spores. Thus, the inventors selected highly pathogenic isolate SLP F2-1, which also produced high amount of spores required for screening peppers for resistance to *Fusarium.*

Initially, the root pathogen discovered in Mexico was thought to be *Phytophthora*, as *Fusarium* was not linked to pepper until the discovery by the inventors was made. Unexpectedly, research knowledge was gained through the identification of the causal agent associated with the wilting symptom of pepper in Mexico and the selection of the *Fusarium oxysporum* f. sp. *capsici* isolates.

In total, 16 lines, provided by breeders along with two pepper lines CM334 and Jupiter, were sown (May 1, 2017) in the greenhouse in Salinas Research Station. Three-weeks-old (May 22, 2017) pepper plants were root dip inoculated ($10^7$ conidia/ml) for 5 min. After inoculation, plants were transplanted into 4×50 cell trays and placed inside growth chamber at 23° C. for 2 week, and later transferred into the greenhouse #1 bench. Plants were evaluated three weeks (Jun. 12, 2017) after inoculation. If sporulation was present, the plant was susceptible; if no sporulation was present, the plant was resistant.

Based on disease evaluation, the two pepper lines: 3960 and XHP12305 were highly resistant. In contrast, two pepper lines (FUS3 and FUS4) were highly susceptible. However, the remaining pepper lines were segregating for resistant and susceptible reactions.

Table 4 shows the results for the reactions of pepper lines produced by the method of the invention to *F. oxysporum* f. sp. *capsici* isolate SLP F2-1. Pepper lines FUS1, FUS2, FUS3, FUS4 and CM334 were susceptible checks. Column 1 shows the pepper line, column 2 shows the number of plants inoculated, column 3 shows the number of plants that were resistant, and column 4 shows the number of plants that were susceptible to infection. No resistant checks were available for *F. oxysporum* f. sp. *capsici* in pepper.

TABLE 4

| Pepper lines | Total plants inoculated | Resistant | Susceptible |
|---|---|---|---|
| FUS1 | 20 | 12 | 8 |
| FUS2 | 20 | 1 | 19 |
| FUS3 | 20 | 0 | 20 |
| FUS4 | 20 | 0 | 20 |
| 3960 | 8 | 8 | 0 |
| 3942 | 8 | 1 | 7 |
| 3934 | 9 | 4 | 5 |
| 4094 | 8 | 3 | 5 |
| 4090 | 9 | 8 | 1 |
| 4045 | 10 | 3 | 7 |
| XHP12305 | 10 | 10 | 0 |
| XHP12286 | 7 | 5 | 2 |
| XHP12179 | 9 | 5 | 4 |
| CM334 | 10 | 0 | 10 |

As shown in Table 4, pepper line 3960, which was produced by the method of the invention, was resistant to infection by *F. oxysporum* f. sp. *capsici* isolate SLP F2-1. Pepper line XHP12305 is a hybrid produced using line 3960 as the male parent, and was also resistant to infection by *F. oxysporum* f. sp. *capsici* isolate SLP F2-1.

Example 5

Pathogenicity Tests to Evaluate Pepper Lines for Resistance to *Fusarium Oxysporum* f. sp. *Capsici* Isolate SLP F2-1

Table 5 shows the results of additional experiments to test reactions of pepper lines produced by the method of the present invention to *Fusarium oxysporum* f. sp. *capsici* isolate SLP F2-1. The experiments were conducted in Salinas, Calif. in 2017. Seedlings were infected at the $2^{nd}$ true leaf stage with SLP F2-1 spores (concentration of $1\times10^7$ conidia/ml) by root dipping method. The roots were soaked in fungal suspension for 15 minutes. The plants were evaluated 3-4 weeks after inoculation. Column 1 shows the date, column 2 shows the line, column 3 shows the cross when the line is a hybrid, column 4 shows the number of plants inoculated, column 5 shows the number of plants that were resistant to infection, column 6 shows the number of plants that were susceptible to infection, column 7 shows the percent resistant, and column 8 shows the percent resistant total. Pepper lines CM334 SAL and CM334 WDL were susceptible checks.

TABLE 5

| Experiment date | Line | Cross | # Inoculated | # Resistant | # Susceptible | % Resistant | % Resistant total |
|---|---|---|---|---|---|---|---|
| 17 May | 3960 | | 8 | 8 | 0 | 100 | 95 |
| 17 Jun | | | 100 | 95 | 5 | 95 | |
| 17 May | 4094 | | 8 | 3 | 5 | 38 | 89 |
| 17 June | | | 66 | 63 | 3 | 95 | |
| 17 June | 4055 | | 100 | 76 | 24 | 76 | 76 |
| | 4098 | | 92 | 84 | 8 | 91 | 91 |
| | 3958 | | 100 | 97 | 3 | 97 | 97 |
| | 4211 | | 94 | 79 | 15 | 84 | 84 |
| | 4222 | | 100 | 99 | 1 | 99 | 99 |
| | 3963 | | | | No germ | | |
| 17 May | XHP12305 | 4094 × 3960 | 10 | 10 | 0 | 100 | 76 |
| 17 June | F2 | | 85 | 70 | 15 | 82 | |
| 17 August | | | 90 | 60 | 30 | 67 | |
| 17 May | XHP12305 | 4094 × 3960 | 10 | 10 | 0 | 100 | 88 |
| 17 June | F1 | | 100 | 84 | 16 | 84 | |
| 17 August | | | 24 | 24 | 0 | 100 | |
| 17 June | FHP12228 | 4055 × 3960 | 58 | 51 | 7 | 88 | 73 |
| 17 August | F2 | | 50 | 28 | 23 | 56 | |
| 17 June | FHP12320 | 4098 × 3960 | 81 | 79 | 2 | 98 | 95 |
| 17 August | F2 | | 62 | 57 | 5 | 92 | |
| 17 June | FHP15137 | 3958 × 3960 | 64 | 57 | 7 | 89 | 81 |
| 17 August | F2 | | 106 | 81 | 25 | 76 | |
| 17 June | FHP15139 | 4211 × 3960 | 100 | 76 | 24 | 76 | 77 |
| 17 August | F2 | | 67 | 53 | 14 | 79 | |
| 17 June | FHP15140 | 4222 × 3960 | 100 | 85 | 15 | 85 | 80 |
| 17 August | F2 | | 73 | 53 | 20 | 73 | |
| 17 June | FHP15147 | 3960 × 3963 | 59 | 58 | 1 | 98 | 89 |
| 17 August | F2 | | 73 | 60 | 13 | 82 | |
| 17 May | CM334 | | 10 | 0 | 10 | 0 | 0 |
| 17 August | SAL | | 36 | 0 | 36 | 0 | |
| 17 August | CM334 WDL | | 30 | 2 | 28 | 7 | |

As shown in Table 5, column 8, inbred pepper lines 3960 and 3958, which were produced by the method of the present invention, showed 95% and 97% resistance to infection by *F. oxysporum* f. sp. *capsici* isolate SLP F2-1, respectively.

Table 6 shows the results of further experiments to test reactions of pepper lines to *Fusarium oxysporum* f. sp. *capsici* isolate SLP F2-1. The experiments were conducted in Salinas, Calif. in June 2018. Seedlings were infected at the $2^{nd}$ true leaf stage with SLP F2-1 spores (concentration of $1\times10^7$ conidia/ml) by root dipping method. The roots were soaked in fungal suspension for 15 minutes. The plants were evaluated 3-4 weeks after inoculation. Column 1 shows the experiment number (no.), column 2 shows the stake number (no.), column 3 shows the entry name, column 4 shows the number of plants inoculated, column 5 shows the number of plants that were resistant to infection, column 6 shows the number of plants that were susceptible to infection, and column 7 shows the percent resistant. Pepper lines 3960, MXP021 and 3958 are pepper plants produced by the method of the current invention.

TABLE 6

| Experiment no. | Stake no. | Entry | No. of plants inoculated | No. of plants resistant | No. of plants susceptible | % resistant |
|---|---|---|---|---|---|---|
| 030518 | 1810 | PPL789 | 52 | 9 | 43 | 17 |
| | 1811 | MXP903 | 40 | 19 | 21 | 48 |
| | 1812 | MXP2001 | 40 | 19 | 21 | 48 |
| 032718 | 1803 | MXP014 | 96 | 22 | 74 | 23 |
| | 1804 | MXP013 | 100 | 4 | 96 | 4 |
| | 1824 | PPL1005 | 90 | 4 | 86 | 4 |
| | 1825 | 3960 | 90 | 80 | 10 | 89 |
| | 1826 | 3960 | 100 | 93 | 7 | 93 |

TABLE 6-continued

| Experiment no. | Stake no. | Entry | No. of plants inoculated | No. of plants resistant | No. of plants susceptible | % resistant |
|---|---|---|---|---|---|---|
| 040218 | 1801 | MXP021 | 32 | 27 | 8 | 84 |
| | 1802 | MXP020 | 89 | 60 | 29 | 67 |
| | 1805 | MXP002 | 100 | 32 | 68 | 32 |
| | 1806 | MXP001 | 100 | 15 | 85 | 15 |
| 61717 | | 3958 | 100 | 97 | 3 | 97 |

As shown in Table 6, inbred pepper line 3960 had 89% and 93% resistance to infection by *F. oxysporum* f. sp. *capsici* isolate SLP F2-1, and inbred pepper lines MXP021 and 3958 showed 84% and 97% resistance to infection by *F. oxysporum* f. sp. *capsici* isolate SLP F2-1, respectively.

Further pathogenicity tests of pepper lines against *Fusarium oxysporum* f. sp. *capsici* isolates and selection and production of pepper lines resistant to *F. oxysporum* f. sp. *capsici* isolates are an aspect of the present invention.

Example 6

Production of *Fusarium Oxysporum* f. sp. *Capsici* Resistant Pepper Line 3960

Inbred pepper line 3960 is resistant to infection by *Fusarium oxysporum* f. sp. *capsici*, including but not limited to *F. oxysporum* f. sp. *capsici* isolate SLP F2-1 and was produced by the method of the present invention. Development of inbred pepper line 3960 began in 2003 with an experimental jalapeño line. $F_2$ seeds were saved from fruit grown in a trial in Agrisales in 2003 and were advanced. Over a number of years, crosses were made and pedigree selection used for advancement. Pathogenicity tests were also performed. In 2017 and 2018, pathogenicity tests were performed and line 3960 (also known as PPL1006 and MXP3012) was confirmed to have resistance to *F. oxysporum* f. sp. *capsici*, including but not limited to isolate SLP F2-1, as shown in Tables 4, 5 and 6 above.

Example 7

Production of *Fusarium Oxysporum* f. sp. *Capsici* Resistant Pepper Line MXP021

Inbred pepper line MXP021 is resistant to infection by *Fusarium oxysporum* f. sp. *capsici*, including but not limited to *F. oxysporum* f. sp. *capsici* isolate SLP F2-1 and was produced by the method of the present invention. Development of inbred pepper line MXP021 began in 2004 in central Mexico. Seed was increased and advanced to the next generation. Over a number of years, pedigree selection and single seed descent were used for advancement and pathogenicity tests were performed. Lines were advanced and selection pressure applied.

In August of 2009, the first combinations of hybrids using MXP021 were generated based on cultural traits, including good seed yielding variety, large size, balanced shape, and good quality mulato (brown colored) poblano. In 2010, new hybrids were tested for adaptation and performance, and at the same time parental lines were increased. In August of 2011, line FHP8256, which is a hybrid that uses MXP021 as the male line, was identified with good potential, and hybrid increased and parental lines were refined over several years.

In 2017 and 2018, pathogenicity tests were performed using *Fusarium oxysporum* f. sp. *capsici* isolates, including isolate SLP F2-1, as in the method of the invention, and XHP8256 (FHP8256) and its pollen parent MXP021 showed resistance to *F. oxysporum* f. sp. *capsici*, including but not limited to isolate SLP F2-1, as shown in Tables 4 and 6 above.

Example 8

Production of *Fusarium Oxysporum* f. sp. *Capsici* Resistant Pepper Line 3958

Inbred pepper line 3958 is resistant to infection by *Fusarium oxysporum* f. sp. *capsici*, including but not limited to *F. oxysporum* f. sp. *capsici* isolate SLP F2-1 and was produced by the method of the present invention. Development of inbred pepper line 3958 was began in 2002. Over a number of years, crosses were made and pedigree selection and single plant selection used for advancement. Lines were advanced and selection pressure applied. Hybrids were created using 3958 and were evaluated, and the line increased. Pathogenicity tests were also performed and showed that line 3958 (also known as PPL1008) was resistant to infection by *Fusarium oxysporum* f. sp. *capsici*, including but not limited to *F. oxysporum* f. sp. *capsici* isolate SLP F2-1, as shown in Tables 5 and 6 above.

Example 9

Method for Producing *Fusarium* Resistant Pepper Lines

The present invention provides for methods of producing a *fusarium* resistant pepper plant, said method comprising:

a) Selecting diseased pepper plants and/or tissue samples;
b) Growing, isolating and purifying disease causing fungus from said selected plants into one or more fungal isolates;
c) Extracting DNA from said isolates and performing PCR;
d) Performing phylogenetic analyses on said DNA to characterize and identify the fungus;
e) Identifying a fungal isolate of *Fusarium oxysporum* f. sp. *capsici* as the disease causing fungus;
f) Performing pathogenicity tests on uninfected pepper plants using said fungal isolate;
g) Selecting pepper plants having resistance to said fungal isolate; and
h) Producing a *fusarium* resistant pepper plant, wherein said plant is resistant to infection by said *F. oxysporum* f. sp. *capsici* isolate.

According to the invention, variations to the above method may be made as needed.

Example 10

Production and Source of *Fusarium Oxysporum* f. sp. *Capsici* Resistant Peppers In another aspect of the invention, *Fusarium oxysporum* f. sp. *capsici* resistant pepper lines were developed by growing large numbers of segregating inbred pepper lines in soils known to have excessive root rot. The *Fusarium oxysporum* f. sp. *capsici* isolates presence was confirmed via plant and soil analysis. Continuous selection pressure every year for 3-4 years resulted in highly resistant lines.

In another aspect, the invention relates to production of inbred *F. oxysporum* f. sp. *capsici* resistant pepper lines. Production of inbred lines with resistance to *F. oxysporum* f. sp. *capsici* was obtained with *fusarium* pathology testing through pedigree breeding using progeny testing, backcrossing or double haploid production of lines derived from crosses involving resistant lines, including MXP021, 3958 and 3960 of the present invention. Unexpectedly, the production of inbred *Fusarium oxysporum* f. sp. *capsici* resistant pepper lines was a difficult hurdle to overcome.

Research suggests that the resistance to *Fusarium oxysporum* f. sp. *capsici*, including but not limited to *F. oxysporum* f. sp. *capsici* isolate SLP F2-1, found in the pepper plants developed by the inventors may be the result of a single dominant gene. The single dominant gene may be a mutant allele that may have additional modifier genes, and is capable of transmitting resistance to *F. oxysporum* f. sp. *capsici* to other pepper plants not containing the gene or mutant allele. As described above for hybrid XHP8256 (FHP8256), crosses made using pepper lines of the invention having resistance to *Fusarium oxysporum* f. sp. *capsici*, including but not limited to isolate SLP F2-1, resulted in hybrid combinations having resistance to *F. oxysporum* f. sp. *capsici*. Additional crosses and experimentation may be performed to determine the presence of a mutant allele as the source of resistance to *F. oxysporum* f. sp. *capsici*, including but not limited to *F. oxysporum* f. sp. *capsici* isolate SLP F2-1. Additionally, genetic markers and/or marker analysis may be used to identify a mutant allele and plants containing said mutant allele. Mapping populations and additional experimentation may also be used to map the gene underlying the resistance to *Fusarium oxysporum* f. sp. *capsici*, including but not limited to *F. oxysporum* f. sp. *capsici* isolate SLP F2-1.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposit Information

Deposits of the Sakata Seed America, Inc. proprietary pepper lines 3960, MXP021, and 3958 disclosed above and recited in the appended claims have been made with the American Type Culture Collection (ATCC), 10801 University Boulevard, Manassas, Va. 20110 under the terms of the Budapest Treaty. The date of deposits was Mar. 26, 2020. The deposits of 625 seeds were taken from the same deposits maintained by Sakata Seed America, Inc. since prior to the filing date of this application. All restrictions will be irrevocably removed upon granting of a patent, and the deposits are intended to meet all of the requirements of 37 C.F.R. §§ 1.801-1.809. The ATCC Accession Numbers are PTA-126732, PTA-126733, and PTA-126731, respectively. The deposits will be maintained in the depository for a period of thirty years, or five years after the last request, or for the enforceable life of the patent, whichever is longer, and will be replaced as necessary during that period.

Deposits of the Sakata Seed America, Inc. *Fusarium oxysporum* f sp. *capsici* isolates SLP F2-2, SLP F2-4, SLP F2-1, SLP F1-4, and SLP F1-2-(4) disclosed above and recited in the appended claims have been made with the Provasoli-Guillard National Center for Marine Algae and Microbiota (NCMA), Bigelow Laboratory for Ocean Science, 60 Bigelow Drive, East Boothbay, Me. 04544 under the terms of the Budapest Treaty. The date of deposits was Jan. 13, 2022. The deposits of fungi were taken from the same deposits maintained by Sakata Seed America, Inc. since prior to the filing date of this application. All restrictions will be irrevocably removed upon granting of a patent, and the deposits are intended to meet all of the requirements of 37 C.F.R. §§ 1.801-1.809. The NCMA Patent Deposit Accession Numbers are 202201004, 202201005, 202201003, 202201007, and 202201006, respectively. The deposits will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A method for selecting a *fusarium* resistant *Capsicum annuum* pepper plant, wherein said pepper plant is resistant to infection by one or more *Fusarium oxysporum* f. sp. *capsici* isolates, said method comprising:

(a) selecting diseased *C. annuum* pepper plants or tissue samples;

(b) growing, isolating and purifying disease causing fungus from said selected plants into one or more fungal isolates;

(c) extracting DNA from said isolates and performing PCR;

(d) performing phylogenetic analyses on said DNA to characterize and identify the fungus;

(e) identifying a fungal isolate of *Fusarium oxysporum* f. sp. *capsici* as the disease causing fungus, wherein said fungal isolate is isolate SLP F2-2, SLP F2-4, SLP F2-1, SLP F1-4, or SLP F1-2-(4), wherein a representative sample of said fungal isolate was deposited under NCMA Accession No. 202201004, 202201005, 202201003, 202201007, and 202201006, respectively;

(f) performing pathogenicity tests on uninfected pepper plants using said fungal isolate; and (g) selecting a *C. annuum* pepper plant having resistance to infection by said *F. oxysporum* f sp. *capsici* fungal isolate.

* * * * *